(12) United States Patent
Millequant et al.

(10) Patent No.: US 6,274,125 B1
(45) Date of Patent: Aug. 14, 2001

(54) GRANULATED COMPOSITION BASED ON PEROXIDIZED DERIVATIVES FOR BLEACHING HAIR AND PROCESS FOR THE PREPARATION OF THE SAID COMPOSITIONS

(75) Inventors: Jean-Marie Millequant, Saint-Maur; Caroline Tricaud, Cormeilles en Parisis; Anne Gaboriaud, Le Raincy, all of (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 08/217,659

(22) Filed: Mar. 25, 1994

(30) Foreign Application Priority Data

Apr. 5, 1993 (FR) .................................................. 93 03994

(51) Int. Cl.⁷ .................................................... A61K 7/135
(52) U.S. Cl. ...................... 424/62; 424/616; 424/DIG. 3; 132/208; 252/94
(58) Field of Search ................................ 424/62, DIG. 3, 424/616; 132/208; 252/94, 102, 117

(56) References Cited

U.S. PATENT DOCUMENTS

| 3,089,824 | | 5/1963 | Wurster . |
| 5,279,313 | * | 1/1994 | Clausen et al. . |
| 5,294,436 | * | 3/1994 | Cope et al. . |

FOREIGN PATENT DOCUMENTS

| 0256127 | 2/1988 | (EP) . |
| 2133983 | 8/1984 | (GB) . |
| 9203120 | 3/1992 | (WO) . |

* cited by examiner

*Primary Examiner*—Raj Bawa
(74) *Attorney, Agent, or Firm*—Nixon & Vanderhye P.C.

(57) ABSTRACT

A granulated composition for bleaching hair compresses granules of a pulverulent material which is sodium persulfate, potassium persulfate, ammonium persulfate, sodium perborate, potassium perborate, ammonium perborate, barium peroxide, strontium peroxide and mixtures thereof bound together with propylene glycol having a molecular weight ranging from 200 to 10,000. The binder is present in an amount not exceeding 25 percent by weight of the composition.

18 Claims, No Drawings

GRANULATED COMPOSITION BASED ON PEROXIDIZED DERIVATIVES FOR BLEACHING HAIR AND PROCESS FOR THE PREPARATION OF THE SAID COMPOSITIONS

The present invention relates to a granulated composition based on peroxidized derivatives, which may be used for bleaching hair, and a process for the preparation of the said composition.

It is known to bleach hair with the aid of a paste obtained by mixing, at the time of application to the hair, a bleaching composition based on peroxidized derivatives with water or, better still, with hydrogen peroxide. The bleaching composition consists, in a known manner, of a peroxidized derivative, generally a persulphate or a perborate of sodium, potassium or ammonium and sometimes a percarboxylic acid salt or a peroxide of, for example, barium or strontium. These compositions also contain, in a known manner, strongly alkaline agents such as alkali metal or alkaline-earth metal metasilicates, phosphates or carbonates; they may also contain other additives: agents for controlling the release of oxygen during the mixing with hydrogen peroxide, such as magnesium carbonate or magnesia; surface-active agents, such as fatty alcohol sulphates, alkyl sulphates and alkylbenzenesulphonates; thickening agents, such as cellulose derivatives, for example carboxymethyl cellulose, starch and its derivatives, guar gum, xanthan gum and alginates; blue or violet colouring agents and perfumes. Such bleaching compositions are described, for example, in "The science of hair care" by C. Zviak, Marcel Dekker Inc. 1986, pages 225 and 226.

The bleaching composition is often used in the form of a powder of small particle size, which makes possible an easy and rapid dissolution in hydrogen peroxide. However, these pulverulent compositions have several disadvantages. In the first place, the pulverulent compositions consist of powders having different apparent densities and, in the course of their handling and their storage, separation of the constituents occurs, the heavier collecting at the lower part of the packaging in which the composition is contained and the lighter in the upper part; as a consequence, during withdrawal of the composition in order to mix it with hydrogen peroxide, the volumes taken at the upper part of the packaging and those taken at the lower part have different compositions and, therefore, a different bleaching power. In the second place, the compositions in pulverulent form give off, during their handling, dusts which contain peroxidized derivatives and are, as a consequence, strongly irritating to the lungs.

In order to resolve this problem, it has already been proposed to place the bleaching composition in granulated form.

According to WO-A 92/03120, it has been proposed to granulate a persulphate and to mix it with optionally granulated particles of the various other constituents of the composition. Granulation of the persulphate may be performed either by spraying and drying an aqueous persulphate solution optionally containing surface-active agents or water-soluble thickening agents, or by spraying a solution of surface-active agent or of thickening agent onto a moving bed of solid persulphate. If this process, as presumed, makes it possible to avoid the formation of irritating persulphate dusts, it certainly does not make it possible to resolve the problem of the separation of the particles of the various constituents of the bleaching composition.

In FR-A 2,044,324, it has been proposed to granulate the constituents of the pulverulent bleaching composition collectively with the aid of a binder: polyvinylpyrrolidone or glucose dissolved in an aqueous, aqueous-alcoholic or alcoholic medium. The problem of the separation of the various constituents of the bleaching composition is thereby resolved, since the various constituents are present in the same granule. However, it has been observed that the use of polyvinylpyrrolidone alone as binder gives hard, but nevertheless crumbly, granules which, on repeated rubbing, form fine dusts which are capable of being carried into the atmosphere in particular at the time of use. Furthermore, granules of high particle size between 1 and 6 mm are obtained, which increases the dissolution time and gives, on mixing with hydrogen peroxide, a paste which remains granular for a long time and the application of which is unpleasant; furthermore, on application to hair this paste runs the risk of giving inhomogeneous and non-reproducible bleaching. In order to improve the use of the granules obtained according to FR-A 2,044,324, it has been attempted to grind them, but irritant dusts are formed in the course of the grinding. In addition, grinding increases the cost of the granules.

According to the present invention, it has been found that by using a specific binder, namely a polypropylene glycol of determined molecular weight, optionally mixed with at least one polyalkylene glycol having a $C_2$ or $C_4$ alkylene group of determined molecular weight, granules are obtained which form practically no dust by rubbing. In addition, granulation makes it possible to obtain granules of particle size between 65 $\mu$m and 800 $\mu$m in higher yield, these granules dissolving readily in hydrogen peroxide to give a homogeneous and creamy paste which is easy to apply to hair. In addition, it should be noted that it is possible to grind the granules having a particle size greater than 800 $\mu$m without any irritant dust being formed.

As a consequence, the subject of the present invention is a granulated composition based on peroxidized derivatives which may be used for bleaching hair, in which the granules have been obtained by granulation of a mixture of its various pulverulent constituents by means of a binder, characterized in that the said binder comprises polypropylene glycol of molecular weight between 200 and 10,000, preferably between 2,000 and 8,000, the granules having a particle size between 65 $\mu$m and 800 $\mu$m.

According to the present invention, polypropylene glycol may be used as a binder, alone or mixed with a small quantity of at least one polyalkylene glycol having a $C_2$ or $C_4$ alkylene group (hereinafter called "$C_2$ or $C_4$ polyalkylene glycol") of molecular weight between 200 and 30,000;the polyalkylene glycol may thus be polyethylene glycol and/or polybutylene glycol. The polyethylene glycol preferably has a molecular weight between 200 and 4,000, and the polybutylene glycol has a molecular weight between 200 and 30,000.

According to the invention, the overall binder concentration (polypropylene glycol alone or mixture of polypropylene glycol and $C_2$ or $C_4$ polyaklylene glycol(s)) preferably does not exceed 25% by weight relative to the total weight of the composition. The polypropylene glycol concentration is advantageously between 10 and 20% by weight relative to the total weight of the composition. The concentration of $C_2$ or $C_4$ polyalkylene glycol(s) mixed with polypropylene glycol preferably does not exceed 5% by weight relative to the total weight of the composition.

According to the invention, the granulated composition must have a particle size between 65 $\mu$m and 800 $\mu$m. In fact, when the particle size is greater than 800 $\mu$m the granules begin to dissolve in the hydrogen peroxide with difficulty and their dissolution cannot be made complete; the paste obtained is granular and not homogeneous. When the composition has a particle size lower than 65 µm, irritant dusts are formed during the handling of the bleaching composition in granulated form.

According to the present invention, it has also been found that easier dissolution in hydrogen peroxide is achieved for granulated compositions containing at least one lubricating agent from the family of cellulose derivatives, preferably sodium carboxymethyl cellulose or hydroxypropylmethyl cellulose and/or at least one lubricating agent from the family of alkali metal or alkaline-earth metal or polyol stearates. The polyol stearates are preferably chosen from glycol stearate and glycerol stearate. A mixture of potassium stearate and glycerol stearate is preferably used. In fact, in the presence of lubricating agent(s), the granules are less hard and less crumbly. The quantity of cellulose derivative (s) present as lubricant is advantageously between 1 and 10% by weight relative to the total weight of the composition, preferably 2 to 6%; the quantity of stearate(s) present is advantageously between 0.1 and 5% by weight relative to the total weight of the composition, preferably 0.2 and 1%; the overall quantity of lubricating agent is advantageously between 1 and 10% by weight relative to the total weight of the composition.

Another subject of the present invention is a process for the preparation of the granulated composition defined above, characterized in that a moving bed of the various pulverulent constituents of the mixture to be granulated is prepared and propylene glycol, which is optionally mixed with at least one $C_2$ or $C_4$ polyalkylene glycol, is sprayed in the form of a solution in a solvent onto the moving bed, and the solvent is removed.

This process makes it possible to obtain granules of more homogeneous particle size and, in particular, to avoid the formation of fines having a particle size lower than 65 µm. The quantity of granules having a particle size greater than 800 µm may be low but, in any case, if they are present in a significant quantity, these granules can be reground virtually without irritant dusts being produced. In order to regulate the particle size to the desired value, the granulation time may be altered. The latter is suitably between 3 and 15 minutes.

The solvent may be any solvent which is compatible with the binder which is dissolved therein. Nevertheless, the use of an aqueous medium (water or an aqueous-alcoholic medium for example) is avoided because the presence of water may initiate decomposition of the peroxidized derivatives and, when the bleaching composition contains an ammonium derivative (for example ammonium persulphate), may result in release of ammonia. The solvent is preferably a $C_1$–$C_4$ alkanol, methylene or ethylene chlorides, or mixtures of these compounds.

The moving bed for the pulverulent mixture onto which the binder solution is sprayed may be any moving bed known for granulation: it may be a bed obtained in a tank with the aid of stirrers, especially blades or beaters, a bed obtained in a rotating drum or a bed obtained with the aid of a stream of ascending gas, such as a fluidized bed.

The pulverulent mixture is preferably homogenized before spraying of the binder solution. This homogenization may be carried out in a subsidiary mixer or in the moving bed before spraying. For example, in the case where the granulation is carried out in a tank, all the pulverulent constituents of the mixture are introduced into the tank and the mixture is homogenized by stirring in the tank before spraying the binder solution, and the stirring is continued, after having modified the conditions, where appropriate, in order to maintain the mixture to be granulated in the form of a moving bed during the spraying and granulation. When granulation is carried out on a fluidized bed, the pulverulent mixture to be granulated may be homogenized by stirring in a subsidiary tank, before introduction of the said mixture into the fluidized bed granulator.

The granulation may be carried out in discontinuous or in continuous fashion.

After granulation a separation is carried out, where appropriate, on the one hand of the fines having dimensions less than 65 µm, it being possible for these fines to be recycled, and on the other hand of the particles having dimensions greater than 800 µm, which are ground without resulting in formation of irritant dusts; the product obtained after grinding and classification is introduced, according to its particle size, either into the pulverulent mixture or into the finished product.

The examples below, given by way of illustration and without any limitation whatsoever being implied, will allow a better understanding of the invention.

EXAMPLES 1 and 2

1) Preparation of the granulates

A "ROTO 50 P" granulator marketed by the Italian company "ZANCHETTA & C" is used, containing a 50-litre tank fitted with a lid equipped with rotating knives and a spraying nozzle, and fitted with a three-blade stirrer at the bottom of the tank, a jacket, a vacuum pump and a system for tipping the tank by ±90°.

13.5 kg of the pulverulent mixture to be granulated are introduced into the tank. The composition of the mixture to be granulated is given in the first eleven lines of Table I below. The mixture is homogenized for 5 minutes with the aid of a three-blade stirrer rotating at 200 revolutions/minute and knives turning at 1000 revolutions/minute. The knives are stopped and the stirring is continued with the aid of the three-blade stirrer after having brought its rotation speed to 160 revolutions/minute.

During this time, a solution of polypropylene glycol (PPG) of molecular weight 2000 or 6000 respectively for Examples 1 and 2, in dichloromethane is prepared; this solution is constituted by mixing 1.5 kg of PPG for 1 litre of solvent.

As soon as the knives have been stopped as indicated above the solution of PPG is sprayed onto the particle bed contained in the granulator in order to add 1.5 kg of PPG to the pulverulent mixture.

When the spraying is finished, the rotation speed of the three-blade spinner is brought to 200 revolutions/minute and the knives are made to rotate at 1200 revolutions/minute until a power surge for the stirrer motors is obtained, which corresponds to the end of the granulation.

The vacuum pump is switched on, the granulator is tipped up by 90° (the axis of the tank is then almost horizontal) and the jacket is heated in order to obtain a temperature which does not exceed 40° C. in the granule bed and to remove the solvent.

2) Tests on the Granules Obtained

When the removal of the solvent is completed the following tests are carried out:
  a) Measurement of the particle size in the calibration apparatus marketed under the name "FC" by the Italian company "ZANCHETTA & C"
  b) Test of the dissolution of the grains:
  10 g of granulated bleaching powder are taken and placed into a non-metallic bowl. It is made into a paste with 10 g of 30-volume hydrogen peroxide, using a spatula. The total dissolution time is determined by observation with the naked eye of the paste obtained, the maximum time being 30 minutes.

c) Measurement of the "volatility" 10 g of granulated powder from the various samples of granulated powder are weighed into glass pots.

Stirring is carried out in the same manner (three complete cycles from low to high and vice versa) and the dust cloud which remains is evaluated visually by taking into account the density of the cloud, its persistence and the size of the particles in suspension. A volatility scale is defined which ranges from 0 to 5, the value 0 corresponding to a non-volatile powder and 5 to a very volatile powder.

The results for these various tests are given in the last three lines of Table I below.

EXAMPLES 1 AND 2

TABLE 1

| Starting materials | Example 1 | Example 2 |
| --- | --- | --- |
| Potassium persulphate | 45 | 45 |
| Sodium persulphate | 7.5 | 7.5 |
| Anhydrous sodium metasilicate | 11 | 11 |
| Ammonium chloride | 5 | 5 |
| Ethylenediaminetetraacetic acid | 1 | 1 |
| Guar gum | 1 | 1 |
| Hydrophilic silica | 3 | 3 |
| Mixture of glycerol stearate and potassium stearate (93/7 by weight) | 0.5 | 0.5 |
| Sodium carboxymethyl cellulose | 1.7 | 1.7 |
| Titanium oxide | 0.5 | 0.5 |
| Colloidal silica | 13.8 | 13.8 |
| PPG (molecular weight = 2,000) | 10 | — |
| PPG (molecular weight = 6,000) | — | 10 |
| Mean particle size (in $\mu$m) | 200 | 200 |
| Dissolution time (min) | 6 | 5 |
| Volatility | 0.5 | 0.5 |

EXAMPLES 3 and 4 (comparative)

Comparative tests were carried out with powders granulated by the process described for Examples 1 and 2, using as the pulverized binder a polyvinylpyrrolidone (PVP) and a polyethylene glycol (PEG) respectively for Examples 3 and 4. The same tests as in Examples 1 and 2 were carried out on the granules obtained. The formulation of the granulated composition is given in % by weight and the results of the tests are given in Table II below:

TABLE II

| Starting materials | Example 3 | Example 4 |
| --- | --- | --- |
| Potassium persulphate | 40 | 50 |
| Sodium persulphate | 9 | 7.5 |
| Anhydrous sodium metasilicate | 10 | 10.8 |
| Ammonium chloride | 5 | 4 |
| Ethylenediaminetetraacetic acid | 2 | 1 |
| Guar gum | — | 1 |
| Hydrophilic silica | — | 3 |
| PVP (molecular weight = 40 000) | 12 | — |
| PEG (molecular weight = 400) | — | 12 |
| Sodium carboxymethyl cellulose | 5 | — |
| Mixture of glycerol stearate and potassium stearate (93/7 by weight) | — | 0.5 |
| Colloidal silica | 17 | 10.2 |
| Particle size (in $\mu$m) | >1000 | 65 to 1000 |

TABLE II-continued

| Starting materials | Example 3 | Example 4 |
| --- | --- | --- |
| Dissolution time (min) | >60 | 30 |
| Volatility | 1 | 1.5 |

These tests show that when a binder other than PPG is used the dissolution time of the granules is higher, the particle size of the granules is too high or too dispersed and the formation of dust is relatively high.

What is claimed is:

1. A granulated composition for bleaching hair comprising granules of a pulverulent material comprising a member selected from the group consisting of sodium persulfate, potassium persulphate, ammonium persulfate, sodium perborate, potassium perborate, ammonium perborate, barium peroxide, strontium peroxide and mixtures thereof, said granules having a particle size ranging from 65 $\mu$m to 800 $\mu$m and being bound together with a binder consisting essentially of polypropylene glycol having a molecular weight ranging from 200 to 10,000, said binder being present in said composition in an amount not exceeding 25 percent by weight based on the total weight of said composition.

2. The granulated composition of claim 1 wherein said polypropylene glycol has a molecular weight ranging from 200 to 8,000.

3. The granulated composition of claim 1 wherein said binder also contains a polyalkyleneglycol having a $C_2$ or $C_4$ alkylene group.

4. The granulated composition of claim 3 wherein said polyalkyleneglycol having a $C_2$ alkylene group is a polyethylene glycol having a molecular weight ranging from 200 to 4,000.

5. The granulated composition of claim 3 wherein said polyalkyleneglycol having a $C_4$ alkylene group is a polybutylene glycol having a molecular weight ranging from 200 to 30,000.

6. The granulated composition of claim 1 wherein said binder is present in an amount ranging from 10 to 20 percent by weight based on the total weight of said composition.

7. The granulated composition of claim 3 wherein said polyalkyleneglycol having a $C_2$ or $C_4$ alkylene group is present in an amount not exceeding 5 percent by weight based on the total weight of said composition.

8. The granulated composition of claim 1 containing at least one lubricating agent selected from the group consisting of a cellulose compound and a stearate compound.

9. The granulated composition of claim 8 wherein said cellulose compound is selected from the group consisting of sodium carboxymethyl cellulose and hydroxypropylmethyl cellulose.

10. The granulated composition of claim 9 wherein said cellulose compound is present in an amount ranging from 1 to 10 percent by weight based on the total weight of said composition.

11. The granulated composition of claim 8 wherein said stearate compound is selected from the group consisting of an alkali metal stearate, an alkaline-earth metal stearate and a polyol stearate.

12. The granulated composition of claim 11 wherein said stearate compound is present in an amount ranging from 0.1 to 5 percent by weight based on the total weight of said composition.

13. A process for preparing a granulated composition for bleaching hair comprising granules of a pulverulent material comprising a member selected from the group consisting of sodium persulfate, potassium persulfate, ammonium persulfate, sodium perborate, potassium perborate, ammonium perborate, barium peroxide, strontium peroxide and mixtures thereof, said process comprising preparing a moving bed of said pulverulent material so as to granulate said pulverulent material, spraying on said moving bed of said pulverulent material a binder consisting essentially of polypropylene glycol having a molecular weight ranging from 200 to 10,000, said binder being in the form of a solution in a solvent selected from the group consisting of a $C_1$–$C_4$ alcohol, methylene chloride, ethylene chloride and mixtures thereof, and removing said solvent so as to produce said granules of said granulated composition, said granules having a size ranging from 65 μm to 800 μm and said binder being present in an amount not exceeding 25 percent by weight based on the total weight of said composition.

14. The process of claim 13 which includes homogenizing said pulverulent material prior to spraying said pulverulent material with said solution of said binder.

15. The process of claim 13 wherein said binder also contains a polyalkyleneglycol having a $C_2$ or $C_4$ alkylene group.

16. The process of claim 15 wherein said polyalkyleneglycol having a $C_2$ alkylene group is a polyethyleneglycol having a molecular weight ranging from 200 to 4,000.

17. The process of claim 13 wherein said polyalkylene glycol having a $C_4$ alkylene group is a polybutylene group having a molecular weight ranging from 200 to 30,000.

18. The process of claim 13 wherein said pulverulent material includes a lubricating agent selected from the group consisting of a cellulose compound and a stearate compound.

* * * * *